US00PP08361P

United States Patent [19]

Warriner

[11] Patent Number: Plant 8,361

[45] Date of Patent: Sep. 7, 1993

[54] ROSE PLANT JACRITE

[75] Inventor: William A. Warriner, Tustin, Calif.

[73] Assignee: Bear Creek Gardens, Inc., Medford, Oreg.

[21] Appl. No.: 795,958

[22] Filed: Nov. 21, 1991

[51] Int. Cl.[5] ..... A01H 5/00

[52] U.S. Cl. ..... Plt./11

[58] Field of Search ..... Plt. 11, 12, 22

*Primary Examiner*—Howard J. Locker

*Assistant Examiner*—E. F. McElwain

*Attorney, Agent, or Firm*—Klarquist, Sparkman, Campbell, Leigh & Whinston

[57] ABSTRACT

A hybrid tea rose created by crossing an unnamed seedling with the variety JACjel, U.S. Plant Pat. No. 4,438, is characterized by the change in its abundant flowers from bright yellow to red as the flower matures, the presence of glands on the peduncles, sepal and stipules and its pleasant, moderate fragrance.

1 Drawing Sheet

The present invention relates to a new and distinct variety of rose plant of the hybrid tea class which was originated by me by crossing the variety an unnamed seedling, with the variety JACjel, U.S. Plant Pat. No. 4,438.

The primary objective of this breeding was to produce a new rose variety having the strong upright growth and orange and yellow flower color of the unnamed seedling combined with the large flowers and heavy flowering of the yellow hybrid tea JACjel. The objective was substantially achieved along with other desirable improvements as evidenced by the following unique combination of characteristics which are outstanding in the new variety and which distinguish it from its parents, as well as from all other varieties of which I am aware:

1. Bright yellow changing to red as the flower matures;
2. Presence of glands on peduncles, sepals and stipules;
3. Pleasant, moderate fragrance;
4. Abundance of flowers.

Asexual reproduction of this new variety by budding, as performed at Wasco and Somis, Calif. shows that the foregoing characteristics and distinctions come true to form and are established and transmitted through succeeding propagations.

The accompanying photograph shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—JACjel, U.S. Plant Pat. No. 4,438.

Classification:

*Botanical.*—*Rosa hybrida.*

*Commercial.*—Hybrid tea.

FLOWER

Observations made from specimens grown in a garden environment in Somis, Calif. in May-Aug. of 1991.

Blooming Habit: Recurrent.

Bud:

*Size.*—1½ inches when the petals start to unfurl.

*Form.*—Long, pointed ovoid.

*Color.*—When sepals first divide, bud color is Yellow Group 6A with Red Group 45D on the side of the flower bud facing the afternoon sun. When half blown, the upper sides of the petals are Yellow Group 6C with the outer petals Red Group 40D except at the petal base where it is Yellow Group 6C. On the lower sides of the petals, the inner petals are Yellow Group 6C while the outer petals are Red Group 40D, except at the petal base where they are Yellow Group 6C.

*Sepals.*—Color: Green Group 138B. Surface texture: Covered in fine hairs. There are three normally appendaged sepals. There are two unappendaged sepals with hairy edges.

*Receptacle.*—Color: Green Group 139C. Shape: Apple. Size: Average, ⅜"×½". Surface: Smooth.

Peduncle.—Length: Medium, 2" long. Surface: Glandular. Color: Bronzy. Strength: Stiff, erect.

Bloom:

*Size.*—Large. Average open size is 4½-5 inches.

*Borne.*—Singly.

*Stems.*—Medium, 14" to 18".

*Form.*—When first open: High centered. Permanence: Retains its form to the end, outer petal edges curl slightly.

*Petalage.*—Number of petals under normal conditions: 25

*Color.*—The upper side of the petals is Yellow Group 6C on the inner petals. On the reverse side of the petals, the inner petals are Yellow Group 6C while the outer are Red Group 40D, except at the petal base where they are Yellow Group 6C. The base of the petals is Yellow Group 6C. The major color on the upper side is Yellow Group 6C.

*Variegations.*—None.

*Discoloration.*—The general tonality at the end of the first day: Slow change form Yellow Group 6C to Red Group 40D. By the end of the third day, there is a gradual spread of the color Red Group 40D which continues until by the sixth day the entire upper surface of the petals is Red Group 40D, except near the petal base.

*Fragrance.*—Moderate.

Petals:

*Texture.*—Thick.

*Shape.*—Deltoid.

*Form.*—Tips slightly recurved.

*Arrangement.*—Imbricated, with a few petaloids in the center.

*Persistence.*—Drop off cleanly.

*Lastingness.*—On the plant: Long, 5–7 days. As a cut flower: Long, 7–8 days.

Reproductive parts:

*Anthers.*—Size: Medium. Quantity: Many. Color: Yellow. Arrangement: Regular around styles, mixed with occasional petaloids.

*Filaments.*—Color: Reddish brown.

*Pollen.*—Color: Gold-yellow.

Styles.—Color: Red.

*Stigmas.*—Color: Greenish-white.

Form: Bush.

Growth: Vigorous; upright; branching.

Foliage:

*Number of leaflets on normal mid-stem leaves.*—5 or 7.

*Size.*—Medium, 5″×4″.

*Quantity.*—Abundant.

*Color.*—New foliage: Reddish. Old foliage: Dark matte green.

Leaflets:

*Shape.*—Pointed oval.

*Texture.*—Upper side: Leathery, smooth.

*Edge.*—Serrated.

*Serration.*—Single, small.

*Petiole rachis.*—Color: Green.

*Petiole underside.*—Rough, with prickles. *Stipules*-.—Medium, bearded and edged with glands.

*Disease resistance.*—Susceptible to mildew but resistant to rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked slightly downward.

*Color when Young.*—Red.

Small prickles:

*Quantity.*—On main stalks: None.

I claim:

1. A new and distinct variety of rose plant of the hybrid tea class, substantially as herein shown and described, characterized particularly as to novelty by the unique combination of its dramatic flower color change from yellow to red, the presence of glands on peduncles, sepals and stipules, its abundance of flowers and its pleasant fragrance.

* * * * *

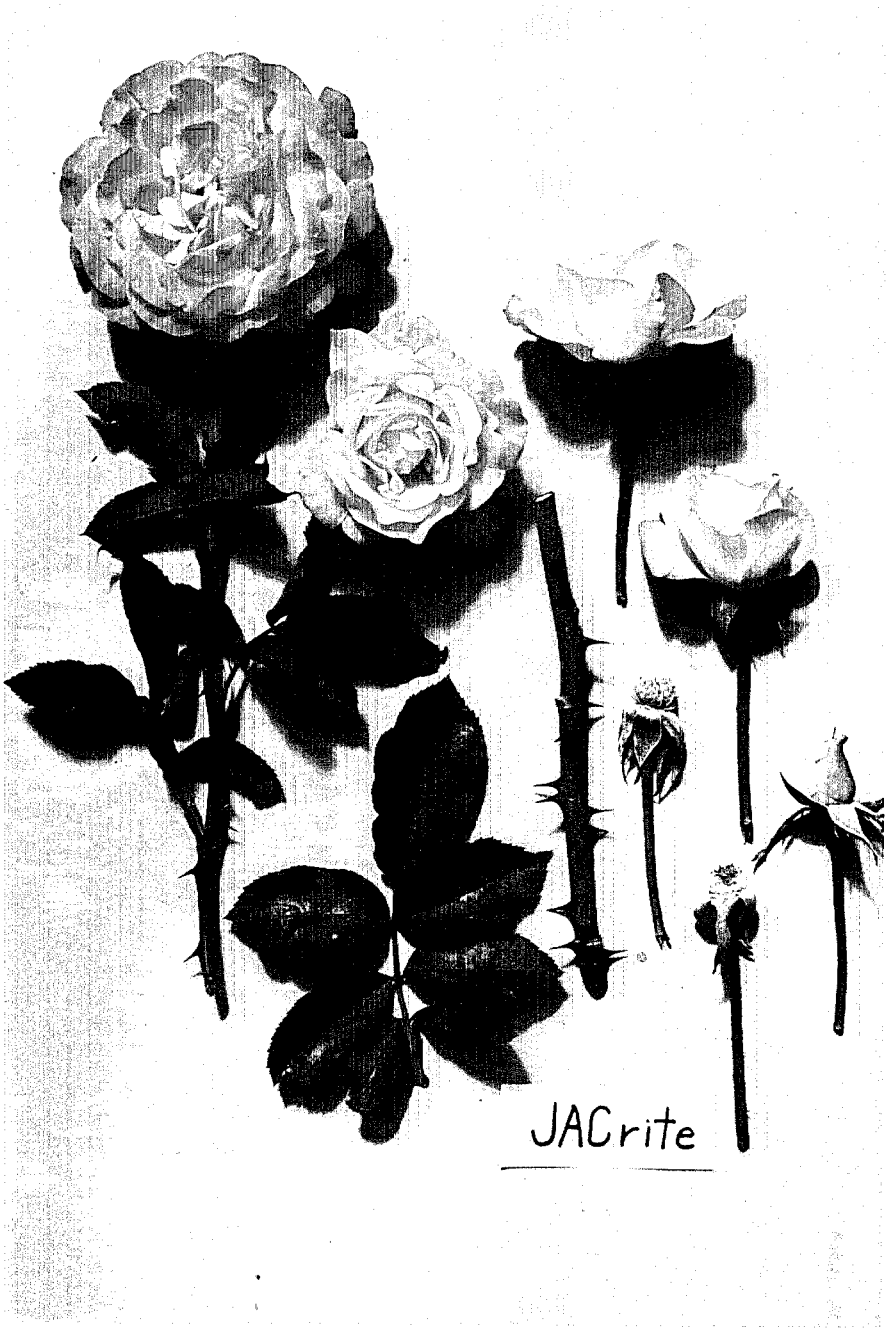
JACrite